United States Patent [19]

Flammang et al.

[11] Patent Number: 4,917,115
[45] Date of Patent: Apr. 17, 1990

[54] PACING SYSTEM AND METHOD FOR PHYSIOLOGICAL STIMULATION OF THE HEART UTILIZING DOPPLER MEANS

[75] Inventors: David Flammang, Angouleme, France; Alexis C. M. Renirie, Berg En Dal; Malcolm J. S. Begemann, Velp, both of Netherlands

[73] Assignee: Vitatron Medical B. V., Dieren, Netherlands

[21] Appl. No.: 217,239

[22] Filed: Jul. 11, 1988

[51] Int. Cl.[4] .............................................. A61N 1/00
[52] U.S. Cl. ........................ 128/419 PG; 128/661.07
[58] Field of Search ............ 128/419 P, 786, 419 PG, 128/661.02, 661.07, 662.06, 697, 696, 703, 704, 661.04

[56] References Cited

U.S. PATENT DOCUMENTS

| | | | |
|---|---|---|---|
| 3,542,014 | 11/1970 | Peronneau | 128/662.06 |
| 3,825,015 | 7/1974 | Berkovits | 128/419 P |
| 3,903,897 | 9/1975 | Woollons et al. | 128/419 P |
| 3,949,757 | 4/1976 | Sabel | 128/786 |
| 4,319,580 | 3/1982 | Colley et al. | 128/661.07 |
| 4,541,433 | 9/1985 | Baudino | 128/662.06 |
| 4,549,548 | 10/1985 | Wittkampf et al. | 128/419 PG |
| 4,577,634 | 3/1986 | Gessman | 128/419 PG |
| 4,600,017 | 7/1986 | Schroeppel | 128/419 PG |
| 4,706,681 | 11/1987 | Breyer et al. | 128/661.04 |
| 4,708,143 | 11/1987 | Schroeppel | 128/419 PG |
| 4,712,554 | 12/1987 | Garson, Jr. | 128/419 PG |
| 4,712,555 | 12/1987 | Thornander et al. | 128/419 PG |
| 4,770,177 | 9/1988 | Schroeppel | 128/419 PG |

FOREIGN PATENT DOCUMENTS 1024065  6/1983  U.S.S.R. .............................. 128/695

Primary Examiner—Kyle L. Howell
Assistant Examiner—Kennedy J. Schaetzle
Attorney, Agent, or Firm—Woodcock Washburn Kurtz Mackiewicz & Norris

[57] ABSTRACT

A cardiac pacemaker and method of operation of such pacemaker is disclosed comprising a single lead having conventional ventricular pacing and sensing electrode means as well as atrial sensors adapted to be positioned in the patient's atrim without any contact with the atrial wall, for sensing atrial wall movement and for generating information signals representative of the atrial wall movement. The free-floating atrial sensor is utilized in providing information for making a determination of a number of cardiac conditions, including analysis of direction of P waves to determine whether sensed signals are anterograde or retrograde.

12 Claims, 4 Drawing Sheets

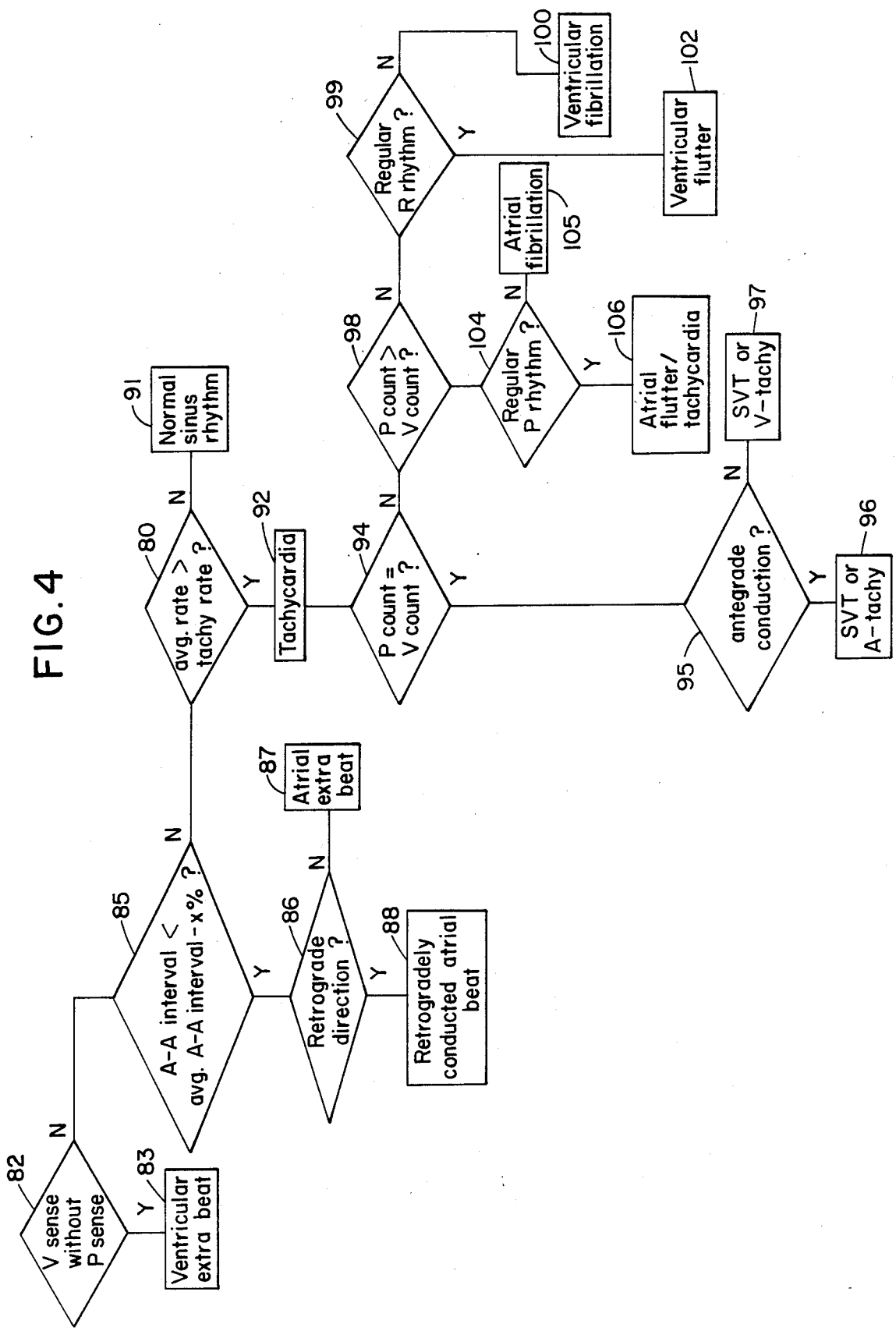

PACING SYSTEM AND METHOD FOR PHYSIOLOGICAL STIMULATION OF THE HEART UTILIZING DOPPLER MEANS

BACKGROUND OF THE INVENTION

Field of the Invention

This invention relates to cardiac pacing devices and, more particularly, devices for treating the heart physiologically by delivering ventricular pacing signals in response to sensed atrial activity.

DESCRIPTION OF THE PRIOR ART

Treatment of patients by implantation of cardiac pacemakers requires a choice of the type of pacemaker to be implanted, meaning that the best possible judgement should be made in terms of the patient condition and the features available from the different technical types of pacemakers. Patient conditions include A-V conduction disorder; cardiac sinus disease; bradytachyatrial syndrome; ventricular tachycardia; and chronic slow atrial flutter. Pacemakers are available in different forms, including single chamber conventional ventricular pacers; rate adaptive ventricular pacers; and dual chamber pacers, including rate adaptive (DDDR) models. In addition, present day programming techniques provide for programming the implanted pacemaker in a large number of different modes.

Experience has shown that a large percentage of the patients who are diagnosed as having A-V conduction disease receive only a single chamber pacemaker, and not a dual chamber pacemaker which can provide DDD or VDD stimulation. This is in spite of the fact that the hemodynamic benefit that can be obtained from the physiological stimulation of a dual chamber pacemaker has been widely demonstrated and acknowledged, particularly in cases of cardiac insufficiency. When ventricular contraction follows atrial contraction, the filling of the ventricle is optimal and heart flow increases from 15 to 30 percent, thus ensuring a better ventricular function and optimal perfusion of the coronary arteries, the brain and all other organs.

Despite medical considerations, a relatively small number of patients currently benefit from the implantation of a dual chamber pacemaker, frequently for secondary considerations other than medical indications, i.e. for technical or other reasons. To a great extent, physicians refuse or decline to implant a dual chamber pacemaker because this requires the installation of two leads, the two leads providing sensing in the atrium and the ventricle respectively. This consideration is not based upon any medical or theoretical conclusion, but because of perceived technical difficulties. In effect the installation of an atrial (auricular) lead requires good dexterity on the part of the physician, since the positioning of the electrode sensor and achieving its attachment at a site where the threshold of sensing and stimulation are optimal are, in practice, found to entail a long, delicate and often difficult procedure.

Numerous systems have been developed in order to attempt an effective improvement in heart flow, by adapting the pacemaking treatment to effort (and to rest) while avoiding the implantation of two leads. The "rate adaptive" pacemaker systems are more physiological than conventional single chamber pacing systems, and provide an improvement in the ventricular function by adapting heart rate to a sensed need of the patient. Such rate adaptive systems include systems based on sensing muscular contraction of the pectoral muscles with the large straight muscles; the Q-T interval; respiratory function; temperature; PH; and others. However, such single chamber rate adaptive pacing systems do not involve auricular contraction and thus do not benefit from the role of the atrium in the diastolic filling.

Thus, in the pacing field today a large number of patients who receive pacemakers, and indeed probably the majority, receive a pulse generator type based upon reasons which are secondary to the underlying cardiac condition. Many of these patients, regardless of their age and cardiovascular pathology, may benefit from the implantation of the dual chamber pacemaker and there thus remains a substantial need in the art to make the advantages of dual pacemaker pacing treatment available to a wider number of potential patients.

SUMMARY OF THE INVENTION

It is an object of this invention to provide a pacemaker system and method which provides the physiological advantages of dual chamber pacing while avoiding the problem of having to implant two separate leads such as heretofore has been required for dual chamber pacemakers.

It is further object of this invention to provide pacemaking apparatus and a method of treatment which enables sensing of the direction and timing of the atrial wall movement, thereby to enable a variety of additional treatments.

In accordance with the above objects, there is provided a cardiac pacemaker/treatment system for VDD pacing, which system comprises a single endocardial lead having a conventional distal portion adapted to be positioned in the ventricle for pacing and sensing, and a portion on the lead which is free floating within the atrium, the free-floating portion having two or more doppler-type sensors for sensing the timing and direction of movement of the atrial wall. The pacemaker apparatus includes logic or analyzing means for receiving the atrial sensor signals as well as the ventricular signal, and for using these input signals to control the pacemaker in VDD operation. Additionally, the timing and direction information is utilized for making a plurality of diagnoses, and for initiating respective treatments responsive to those diagnoses.

BRIEF DESCRIPTION OF THE DRAWINGS

FIG. 4 is a flow diagram illustrating an embodiment of software for determining many of the conditions shown in block 50 of FIG. 2.

DESCRIPTION OF THE PREFERRED EMBODIMENTS

Figure 1:
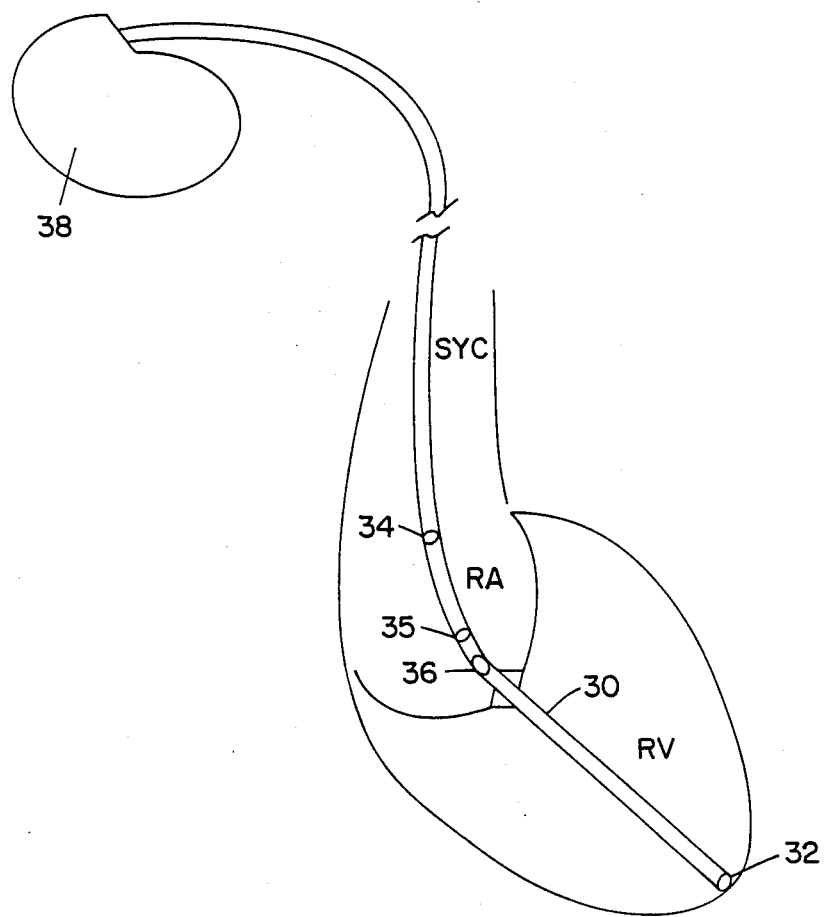
FIG. 1 is a diagrammatic illustration of the single lead of the invention positioned in the heart, the distal tip portion fixed in the apex of the right ventricle, and having at least two atrial sensors positioned on the lead so as to be in the atrium at respective locations for sensing the timing and movement of respective portions of the atrial wall.

Referring to FIG. 1, there is illustrated a single endocardial lead 30 for use in a single chamber or dual chamber pacing system, modified to include means for detecting atrial wall movement. The ventricular electrode 32 is placed at or near the distal tip, for the conventional functions of delivering ventricular pacing signals and for sensing ventricular heartbeats (R-waves). An additional ring electrode, not shown, may be included just proximal to tip electrode 32, for bipolar ventricular pacing and/or sensing. Additionally, there is illustrated at 34 and 35 a pair of atrial sensors for sensing atrial wall movement. A possible third sensor is illustrated at 36, and it is to be understood that a plurality of such atrial sensors may be utilized. The atrial sensors are of a doppler type adapted to determine the timing of atrial wall movement as well as the direction of the movement. Such a doppler sensor may be a Millar Mikro-Tip/doppler transducer. This type of sensor comprises an ultraminiature ring-shaped 20 MHz ceramic crystal capable of being both a transmitter and a receiver of acoustic signals. The ultrasound pulses are transmitted from each sensor and directed toward the atrial wall, and the reflections from the atrial wall provide measurements of the timing, direction, and velocity of the wall movement. It is to be noted that the sensors 34, 35 are free floating on the lead 30 in the sense that there is no need for fixation to the heart wall. They are positioned so as to detect atrial wall movement at respective different atrial wall locations. For example, if a pair of atrial sensors such as illustrated at 34, 35 are utilized, they are preferably positioned at an interelectrode distance d of at least one centimeter and preferably up to 5 centimeter. The optimum distance is believed to be 1-3 cm, but the distance could be up to 10 cm. The distalmost sensor of the atrial sensors should be positioned so as to be 1-3 cm proximal of the tricuspid valve, and thus be in the range of 10-20 cm proximal from the distal tip. In practice, a plurality of atrial sensors may be used, with a test being made at the time of implantation or later to select the two or more electrodes that provide optimum location for accurate sensing of atrial wall movement.

In the pacemaker system of this invention, the lead 30 is connected to pacer 38 by suitable connector means. The lead incorporates wires for delivering required signals from the pacer to the Doppler electrodes and pacing electrode, and for transmitting sensed signals back to the pacemaker.

Figure 2:
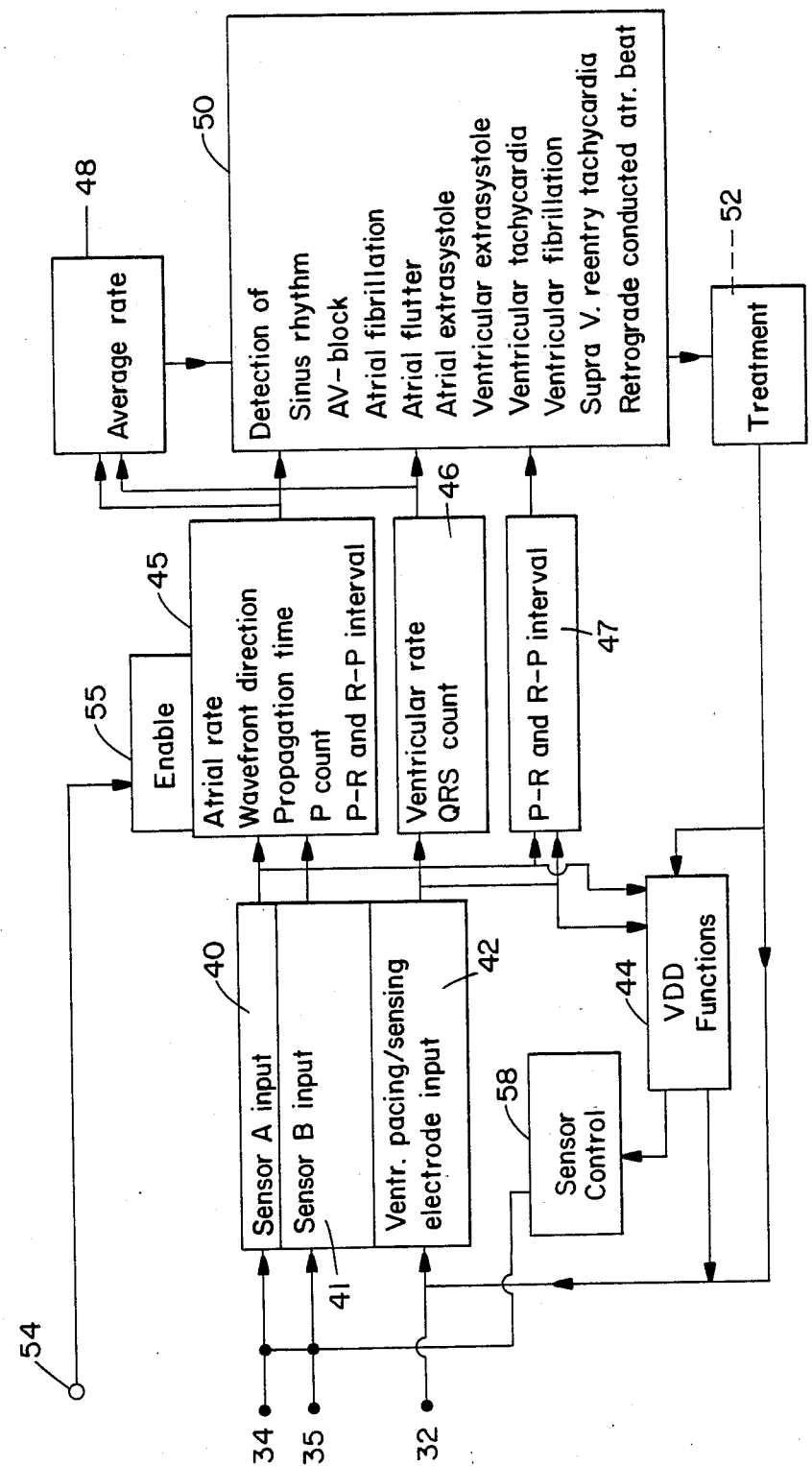
FIG. 2 is a functional block diagram showing the system of this invention, and including designation of sensed signals, heart parameters that are determined and corresponding heart conditions that are detected, and the VDD and supplemental treatment functions that are carried out.

Referring now to FIG. 2, there is shown a block diagram illustrating the information paths of the pacemaker system, as well as the functions that are enabled. As seen, ventricular electrode 32 provides an input signal to V sensor input block 42. The two atrial sensors illustrated 34, 35 provide inputs to A sensor input blocks 40, 41. The doppler sensor devices are controlled through sensor control 58. The outputs of blocks 40, 41, which comprise the conventional means for generating clean signals representative of the sensed signals, are inputted to function block 45. At block 45 the pacemaker determines the following:

(a) atrial rate
(b) atrial wave duration
(c) propagation time
(d) P count (number of atrial contractions)
(e) P-R or R-P' interval These functions are suitably carried out by a microprocessor chip, in a fashion that is well known in the pacing industry. Additionally, these functions may be enabled by the inputting from an extra sensor 54 of a signal into an enable circuit 55. The extra sensor may, for example, be a pressure sensor to provide some other type of indication of heart condition, to enable determination of one or more of these atrial conditions. The pressure sensor may also suitably be carried on lead 30, for sensing atrial contractions.

The V signal is taken from block 42 and inputted into block 46, for determination of V rate and QRS count, in conventional fashion. The V signal is also inputted to block 47, along with at least one of the atrial signals to determine the P-R or R-P' interval. The V signal, and at least one A signal, are also inputted into block 44 for providing basic timing for carrying out the VDD pacemaker functions in a manner well known in pacing industry.

The outputs of blocks 45 and 47 are inputted into block 50, where the apparatus of this invention analyzes the signals for detection of a plurality of heart conditions that are listed in block 50. Also, outputs from blocks 45 and 46 are inputted into block 48, where the average rate is determined and inputted into block 50. With this information, detection of a large number of heart conditions can be made, for the purpose of enabling supplemental treatments. Outputs from block 50 are passed to block 52 for the determination of such supplemental treatments. Output pulses from block 52 are passed directly to the ventricular electrode 32; output signals from block 52 may also be inputted into block 44 for modification of VDD functions as may be necessary.

Figure 3:
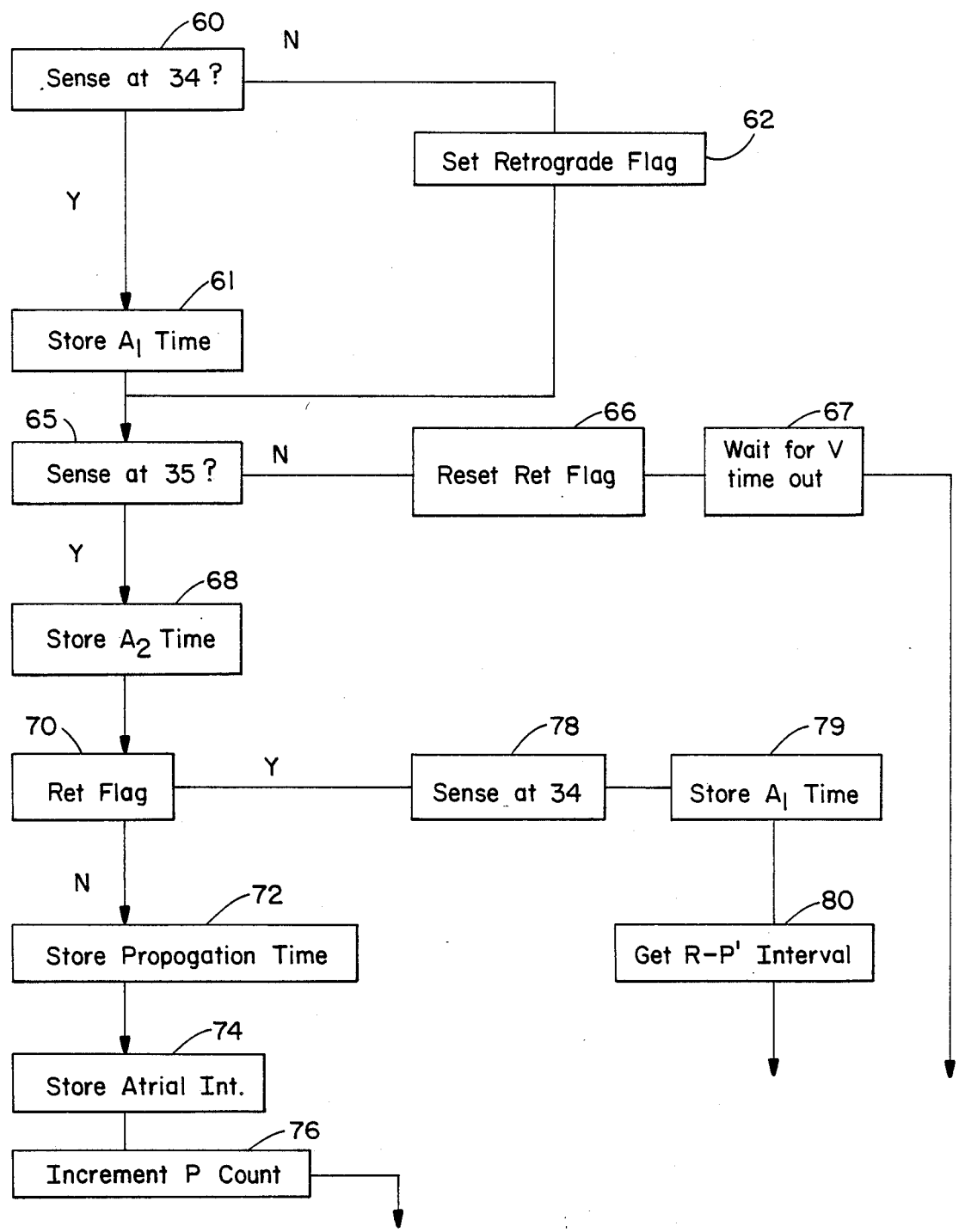
FIG. 3 is an abbreviated flow diagram illustrating an embodiment of this invention for determining whether the atrial signal (P wave) is anterograde or retrograde.

Referring now to FIG. 3 there is shown an abbreviated flow diagram for determining the direction of the atrial signal, i.e., whether it is anterograde or retrograde. In this flow diagram, $A_1$ indicates a first sensor electrode (34) and $A_2$ indicates a second sensor electrode (35). It is assumed that the subprogram is initiated when an atrial signal has been sensed at at least one sensor, or at time out of the atrial escape interval if the pacer has an atrial stimulation mode.

At 60, it is first determined whether a signal has been sensed at 34. If yes, then the time $A_1$ is stored at block 61. If no, this means that the fist signal was sensed at 35, and the retrograde flag is set at 62. The program then proceeds to block 65 where it determines whether there has already been a sense at 35. If yes, the time $A_2$ is stored. If no, then this means that there has been no sensed signal at either atrial sensor and the retrograde flag is reset at block 66; the program then goes to block 67 and waits for V time out. Returning to 65, the program waits to see if an atrial signal will be sensed. If a signal is sensed at 35, then the $A_2$ time is stored and the subprogram proceeds to 70. There it is determined whether the retrograde flag has been set. If no, meaning that there is an anterograde P wave, the propagation time of the atrial wave is stored at 72 (a function of the time between sensing at 34 and 35). Then at 74 the time from the last P wave is determined, and the atrial interval is stored. Then at 76 the pacemaker increments the P count and exists from the subroutine. If, at block 70, the retrograde flag has been set, this means that the signal at 34 has not yet been sensed. As soon as it is, the timing is determined at 78 and the $A_1$ time is stored at 79. Then, at block 80, the program determines the interval from the last R-wave to the timing of the retrograde P wave, getting the R-P' interval.

Directing attention to FIG. 4, there is shown a flow diagram of the embodiment of the invention wherein software is used to carry out determination, i.e. detection of a number of the conditions set forth in block 50. It is to be understood that this flow diagram is illustrative, and the utility of this invention is not limited to the steps shown in the figures. The logical determination can be carried out with a suitably programmed microprocessor. At the beginning of the routine, 82, there is a determination of whether there has been a V-sense without P-sense. If the answer is yes, this means that there has been a ventricular extra beat, or PVC, as indicated at 83. If no, the routine branches to 85, where it is determined whether the most recent A-A interval is less than the accumulated average A-A interval minus a given percentage of that average. This logic is designed to determine whether there has been a very short interval such as would indicate retrograde P wave. This is done at 86. If the answer is no, then it is determined at 87 that there has been an atrial extra beat. If the answer is yes, as indicated at 88, it is determined that there has been a retrogradely conducted atrial beat -P'-, which information can be utilized for carrying out other operations.

Returning to block 85, if no very short interval has been detected, the routine goes on at 90 to determine whether the updated average rate is greater than the preset tachycardia rate. If no, then at 91 it is determined that the patient has normal sinus rhythm. If yes, then at 92 it is determined that tachycardia is present. The routine proceeds to 94, where it is determined whether the P count equals V count. If yes, it is determined whether conduction has been normal, i.e. anterograde. If the answer is yes, then at 96 a determination of SVT (supraventricular tachycardia) or AT (atrial tachycardia) is made. If no, then at 97 there is a determination of SVT or ventricular tachycardia.

Returning to block 94, if P count does not equal V count, then at 98 it is determined whether the P count is greater than the V count. If no, then the routine goes to 99 to determine whether rhythm is regular. If no, then at 100 it is concluded that ventricular fibrillation is present. If yes, then at 102 it is determined that there is ventricular flutter. Returning to 98, if the answer is yes, then at 104 it is determined whether there has been regular P rhythm. If no, at 105 the routine determines that atrial fibrillation is present. If yes, then at 106 it is determined that there is atrial flutter or tachycardia.

In practice, when any of the conditions as set forth in FIG. 4 are determined, the pacemaker can flag these for subsequent determination of supplemental treatment, as indicated at block 52 in FIG. 2. It is to be noted that although the invention has been described particularly with respect to VDD pacing, it can also be used for atrial pacing in a DDD mode. The atrial sensors as utilized in this invention can be utilized, for example, to sense the stimulation-P interval, for purposes of determining desired atrial pacing rate, or to sense the morphology of the atrial contraction to gain information concerning desired atrial rate.

We claim:

1. A cardiac pacemaker/treatment system having a generator device and a lead means, said generator device having a controllable pulse generator for generating pulses, input means for receiving input signals representative of at least cardiac conditions, and logic means for analyzing said input signals and controlling said pulse generator to deliver generator pulses in response to said analyzing, said lead means having a proximal end connected to said generator device and a distal end portion adapted to be positioned in a patient's ventricle for delivering generated pulses to said ventricle and for sensing heartbeats and delivering input signals representative of said heartbeats to said input means,
characterized by said lead means having atrial sensor means adapted to be positioned in the patient's atrium without any contact with the atrial wall for sensing atrial wall movement and for generating atrial input signals representative of the velocity and direction of said wall movement, and said logic means having atrial signal means for analyzing said atrial input signals and controlling the delivery of pulses to the ventricle as a function of said analysis.

2. The system as described in claim 1, wherein said atrial sensor means comprises at least two atrial sensors displaced from each other on said lead means so as to each have a respective ability to track atrial wall movement at respective atrial wall locations.

3. The system as described in claim 2, wherein each of said atrial sensors comprises doppler means for sensing direction of wall movement.

4. The system as described in claim 2, wherein said logic means comprises means for determining from said atrial input signals the amount of wall movement and timing of wall movement at each of said atrial wall locations, whereby to detect the direction and timing of atrial (P) waves.

5. The system as described in claim 2, wherein the distance between two of said atrial sensors is within the range of 1-5 cm.

6. The system as described in claim 5, wherein said distance is within the range of 1-3 cm.

7. The system as described in claim 2, wherein the most distally located of said atrial sensors is adapted to be positioned within 1-3 cm from the tricuspid valve.

8. The system as described in claim 2, comprising an extra sensor adapted to be positioned in the heart for sensing an extra indication of heart function, and means for connecting the output of said extra sensor to said logic means under predetermined heart conditions.

9. The system as described in claim 2, wherein said generator device comprises VDD pacing means for pacing the patient in the VDD mode.

10. The system as described in claim 2, wherein said atrial sensor means comprises three sensor elements each positioned at respective locations on said lead and adapted to track atrial wall movement at respective atrial wall locations, and selection means for selecting the atrial sensor signals to be utilized for said analyzing.

11. The system as described in claim 2, characterized by said lead means having a single endocardial lead having a portion proximal to said distal portion so as to be free-floating within the atrium when said distal end portion is located in the ventricle, said proximal portion having sensor means for sensing the timing and direction of movement of the atrial wall and for generating input signals representative of said timing and movement, and said logic means having analyzing means for analyzing said input signals and controlling the delivery of pulses to the ventricle as a function of said analyzing.

12. A pacing system comprising a pacemaker generator and a single lead connected thereto, said lead having ventricular electrode means for sensing and pacing in patient's ventricle and atrial sensing means for sensing direction of wall movement of the patient's atrium and for generating output signals indicative thereof, said pacemaker generator having means for determining the presence of retrograde P waves solely as a function of output signals.

* * * * *

UNITED STATES PATENT AND TRADEMARK OFFICE
CERTIFICATE OF CORRECTION

PATENT NO. : 4,917,115

DATED : April 17, 1990

INVENTOR(S) : Daniel Flammang; Alexis C.M. Renirie; Malcolm J.S. Begemann

It is certified that error appears in the above-identified patent and that said Letters Patent is hereby corrected as shown below:

ON THE TITLE PAGE item (75):

Please correct the first name of the first inventor to read:

DANIEL FLAMMANG

Signed and Sealed this

Twenty-first Day of July, 1992

Attest:

DOUGLAS B. COMER

*Attesting Officer*     Acting Commissioner of Patents and Trademarks